(12) United States Patent
Ludwig

(10) Patent No.: US 7,268,351 B2
(45) Date of Patent: Sep. 11, 2007

(54) GAS SENSOR MODULE FOR THE SPECTROSCOPIC MEASUREMENT OF A GAS CONCENTRATION

(75) Inventor: Ronny Ludwig, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 107 days.

(21) Appl. No.: 11/113,373

(22) Filed: Apr. 21, 2005

(65) Prior Publication Data

US 2005/0285039 A1 Dec. 29, 2005

(30) Foreign Application Priority Data

Jun. 29, 2004 (DE) ............... 10 2004 031 316

(51) Int. Cl.
*G01N 21/35* (2006.01)
(52) U.S. Cl. .................................. 250/339.13
(58) Field of Classification Search ............ 250/338.1, 250/339.13
See application file for complete search history.

(56) References Cited

U.S. PATENT DOCUMENTS

| | | | | |
|---|---|---|---|---|
| 4,567,006 A | * | 1/1986 | Covington et al. | ......... 264/459 |
| 5,352,851 A | * | 10/1994 | Wallace et al. | ............. 174/529 |
| 5,897,338 A | | 4/1999 | Kaldenberg | |
| 5,962,854 A | * | 10/1999 | Endo | ........................... 250/349 |
| 2004/0074284 A1 | | 4/2004 | Day et al. | |

FOREIGN PATENT DOCUMENTS

| | | |
|---|---|---|
| DE | 10243014 | 3/2004 |
| DE | 10319186 | 11/2004 |
| DE | 10318501 | 1/2005 |
| EP | 1211721 | 6/2002 |
| WO | WO 2004048955 | 6/2004 |
| WO | WO 2004114403 | 12/2004 |

* cited by examiner

*Primary Examiner*—David Porta
*Assistant Examiner*—Marcus H Taningco
(74) *Attorney, Agent, or Firm*—Kenyon & Kenyon LLP

(57) ABSTRACT

A gas sensor module for the spectroscopic measurement of at least one gas concentration, including at least: a spectroscopic gas sensor having a sensor chip which has a micropatterned measuring structure, and having an IR-transparent cap chip covering the measuring structure; a premolded package having a package bottom and a package edge to which a cover having a screen opening provided above the measuring structure is attached; a filter chip provided between the cover and the cap chip; and a lead frame which is partially injected into the premolded package and has multiple leads that include connecting pins for contacting a substrate and contact pads which contact the contact pads of the gas sensor, the connecting pins being bent upward from the package edge. The gas sensor module is mountable by its connecting pins to a substrate in such a way that the measuring structure having the filter chip is positioned directly opposite a substrate opening. Compact dimensions of the finished sensor unit are achieved, while minimizing the production time and ensuring a high degree of radiation shielding.

5 Claims, 2 Drawing Sheets

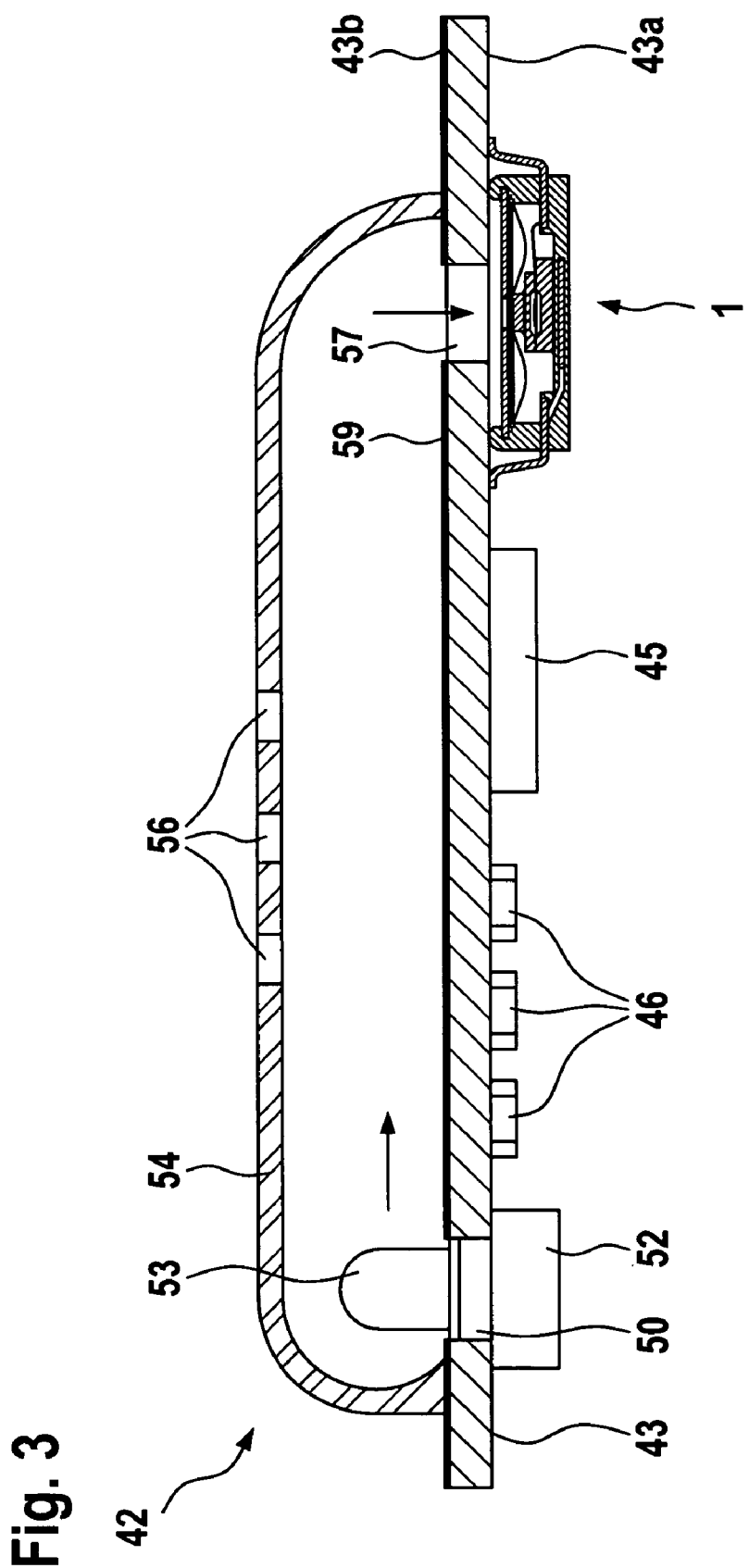

GAS SENSOR MODULE FOR THE SPECTROSCOPIC MEASUREMENT OF A GAS CONCENTRATION

FIELD OF THE INVENTION

The present invention relates to a gas sensor module for the spectroscopic measurement of a gas concentration, which may be used, in particular, in automotive applications.

BACKGROUND INFORMATION

A gas sensor module of this type includes, for example, a premolded package having an injection-molded lead frame that includes multiple leads forming bond pads on the inside of the premolded package and connecting pins on the outside for contacting with a substrate, for example a p.c. board. The gas sensor, which is formed, for example in the form of a chip stack, by a sensor chip having a diaphragm and an infrared-sensitive measuring structure, and a cap chip covering the measuring structure, is generally glued to the bottom of the package and contacted with the lead contact pads via wire bonds. The package interior can be filled with a passivation gel to protect the wire bonds. One or more optical filter chips, which are selectively transparent to IR radiation within certain spectral ranges and thus allow the IR radiation to be measured within a spectral range that is relevant for a specific gas and, for example, a reference spectral range, are attached to the cap chip or the bottom of the cover.

The connecting pins are bent downward so that the bottom of the gas sensor module can be attached to the substrate. An IR lamp, for example an incandescent light bulb which operates in the low-current range, is provided at a lateral distance therefrom, an absorption distance or an absorption chamber being definable between the IR lamp and the gas sensor module, for example by a reflector that is attached to the top of the substrate and reflects the IR radiation emitted by the IR lamp to the gas sensor module. The absorption of the gas or gas mixture in the absorption chamber can thus be used to detect the gas concentration.

Using a standard assembly method, the gas sensor module is mounted on the substrate, on which not only a variety of other structural components, but also the IR radiation source is located at a defined distance from the detector. The reflector is mounted above the lamp and the gas sensor to concentrate the IR radiation. The dimensioning of the sensor package module in the lateral direction and in height substantially determines the minimum reflector size, since the reflector surrounds the gas sensor module.

SUMMARY OF THE INVENTION

The gas sensor module according to the present invention has a plurality of advantages over this design. According to the present invention, the connecting pins of the gas sensor module are bent upward, i.e. away from the package bottom on which the gas sensor module is mounted and toward the top of the package. The gas sensor module is therefore mountable by its connecting pins on the substrate so that the measuring structure including the optical filter chip lies directly opposite the substrate. Because an opening in the substrate is provided above the measuring structure and the filter chip, IR radiation may be conducted through the substrate to the gas sensor attached to the bottom of the substrate. The connecting pins of the premolded package thus face the cover or the opening.

According to the present invention, the reflector size may be substantially reduced, since the gas sensor module does not have to be enclosed beneath the reflector. This makes it possible to greatly reduce the total size of the gas sensor unit.

In addition, all electrical components are mountable on a one-sided substrate in a single process step, in particular without turning over. This substantially reduces the production time by eliminating a two-sided process and improves the quality of the soldered connections due to a one-sided reflow soldering process.

By providing the substrate with a reflective top surface, which may be formed, for example, by metal plating using, for example an NiAu coating, radiation may be reflected from the IR radiation source to the substrate opening via both the reflector and the top of the substrate; this results in a high radiation yield and full coverage of the absorption area formed between the reflector and the substrate. The radiation is therefore not undesirably shielded by the gas sensor module itself. In addition, it is not necessary for the reflector to have an EMC (electromagnetic compatibility) function even if the sensor is sensitive thereto.

As a result, the reflector does not necessarily have to be made of metal, or metal coatings on its interior do not require complex electrical connection to the substrate, as is often the case in conventional systems. The reflective coating on the top of the substrate is easily connectable to the system ground, thus economically providing ideal EMC protection of the gas sensor module located beneath the substrate as well as the remaining electrical components.

Due to the deflection through the substrate and improved coverage of the absorption chamber by the reflective coating on the top of the substrate, the radiation absorption path is also enlarged, which increases measurement accuracy. The steeper incidence angle of the radiation onto the gas sensor module due to the greater distance between the gas sensor module and the reflector is also advantageous.

According to the present invention, it is also possible to use a premolded package that provides good stress relief between the gas sensor chips and the substrate. The shape and dimensions or footprint of the premolded package also remain compatible with the JEDEC (Joint Electron Device Engineering Council) standard. The package may thus be mounted on standard equipment and is suitable for automotive applications.

Using a flat package bottom, the package cover designs may vary specifically, for example, due to openings, grooves and edges without this disadvantageously impairing the ability to mount the gas sensor module on a substrate. According to the present invention, therefore, it is possible to use a very simple standard assembly process, for example a pick-and-place method, for example using vacuum pickup tools, which always employ the same back of the package as the suction surface.

A shielding plate or metallic surface, which is connected to the ground connecting pin of the lead frame, is inexpensively injectable into the bottom of the premolded package. This makes it possible to ensure very good EMC protection due to the additional formation of the reflective layer on the top of the substrate and using a ground connection.

According to the present invention, an electrically active orientation of the gas sensor module with respect to the beam path is possible in the case of a premounted reflector.

BRIEF DESCRIPTION OF THE DRAWING

FIG. 3 shows a cross-section of a gas sensor unit having a substrate, a gas sensor module, a lamp and a variety of electronic components.

DETAILED DESCRIPTION

Figure 1:
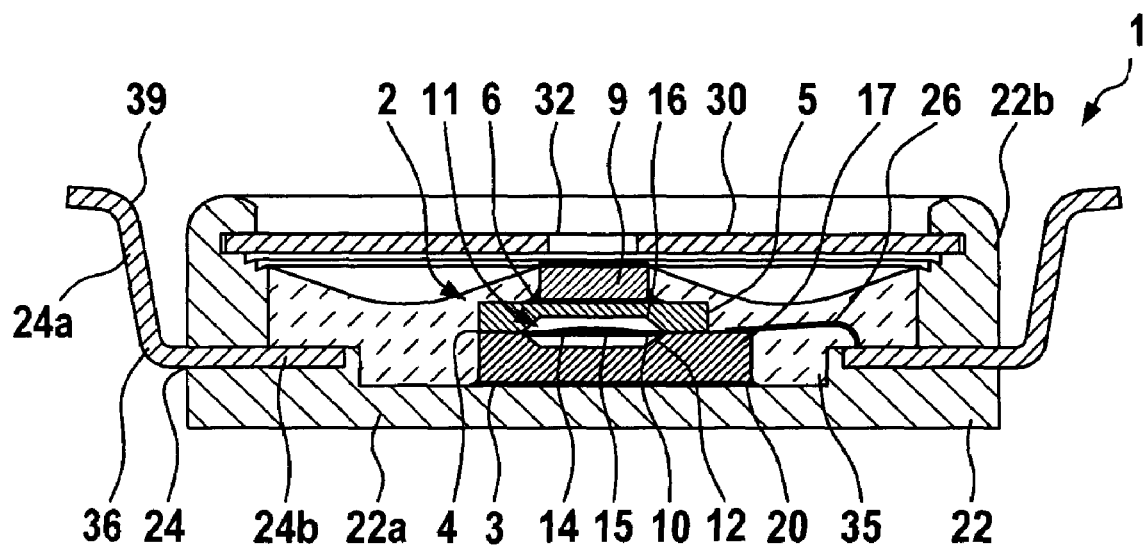
FIG. 1 shows a cross-section of a gas sensor module according to a first embodiment of the present invention.

According to FIG. 1, a gas sensor module 1 includes a gas sensor 2 having a sensor chip 3 and an IR-transparent cap chip 5 which is attached to sensor chip 3 by vacuum-tight seal glass connections 4. An optical filter chip 9 is attached to the top of cap chip 5, using an adhesive layer 6, which is optically transparent to IR radiation.

On the top of sensor chip 3, a measuring structure 11 is provided, which includes a diaphragm 10 that is underetched by a cavity 12 and a also includes a thermopile structure 14 on the diaphragm 10, which, in turn, is covered by an absorber layer 15 to absorb IR radiation. Thermopile structure 14 includes at least printed conductors which are contacted with each other and are made of different materials, for example polycrystalline silicon and a metal, and extends laterally from diaphragm 10 and past diaphragm 10 into the solid edge area of sensor chip 3. The printed conductors of thermopile structure 14 are connected to bond pads 17 provided on the top of sensor chip 3 outside cap chip 5 for the purpose of external contacting. A further cavity 16, which accommodates measuring structure 11, is positioned on the bottom of cap chip 5.

Sensor chip 3 is glued by an adhesive layer 20 to bottom 22a of a premolded package 22 that is injection-molded from a molding compound or plastic material and also has a circumferential edge 22b. A lead frame 23 having multiple leads 24 is partially injected into premolded package 22, outer areas of leads 24 serving as connecting pins 24a, and an inner area of each lead 24 being exposed on its top in the form of a bond pad 24b. In this case, bond pads 24b are contacted with bond pads 17 on the top of sensor chip 3 via wire bonds 26.

Premolded package 22 is closed by a cover 30 made, for example, of metal and having a screen opening 32 that is provided above optical filter chip 9 and therefore serves as a screen for incident IR radiation, which is able to pass vertically through optical filter chip 9, optically transparent adhesive layer 6, cap chip 5 and thus reach absorber layer 15. A passivation means, for example a passivation gel 35, is provided in package interior 34 between premolded package 22 and cover 30.

According to the present invention, connecting pins 24a are bent upward, i.e. in a direction away from the package bottom. They have a curvature 36 in which they are bent upward at an angle from their horizontal position in which they exit a package edge 22b, as well as a second curvature 39 in which they are again bent slightly in the horizontal direction.

Figure 2:
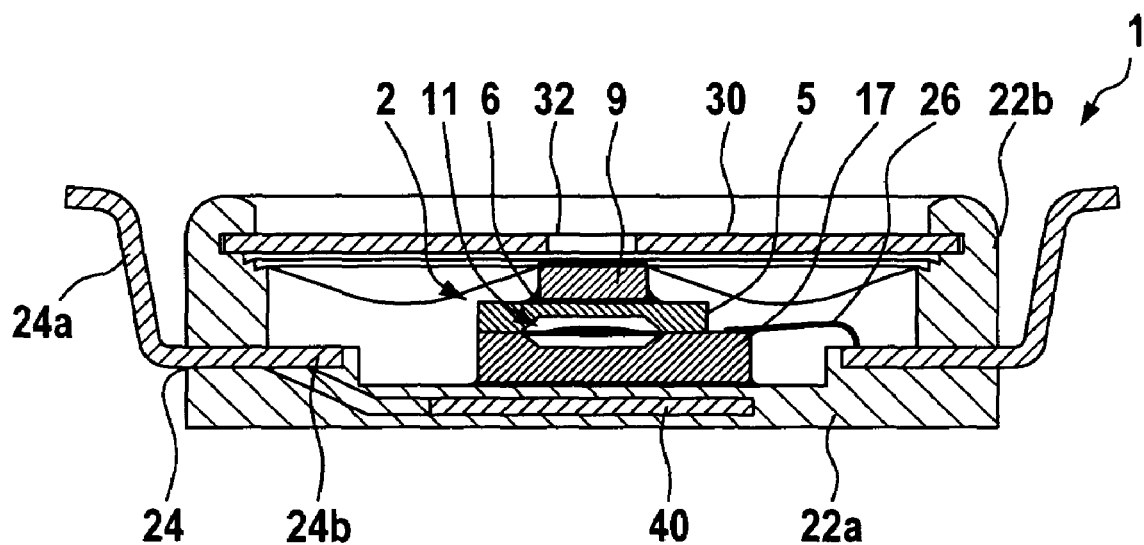
FIG. 2 shows a cross-section of a gas sensor module in a second embodiment having a shielding plate injected into the package bottom.

FIG. 2 shows an embodiment in which a shielding plate 40 is injected into package bottom 22a as part of lead frame 23. Shielding plate 40 is connected to a lead 24 and is therefore connectable to a ground contact of a substrate via corresponding connecting pin 24a.

FIG. 3 shows a gas sensor unit 42 in which a gas sensor module 1 according to FIG. 1 or FIG. 2 is connected by its connecting pins 24a to bottom 43a of a p.c. board 43 serving as a substrate. Printed conductors on which other structural components, preferably a control unit 45, for example an ASIC 45, and passive components 46 are contacted, is provided on bottom 43a of p.c. board 43. A lamp base 52 having a mounted lamp, for example an SMD miniature lamp 53, is inserted through a substrate opening 50 and protrudes beyond top 43b of p.c. board 43. A reflector 54 having gas passage holes 56, which surrounds lamp 53 and a substrate opening 57 above screen opening 32 in gas sensor module 1, is also attached to top 43b. Within the area enclosed by reflector 54, a reflective substrate coating 59, for example made of NiAu, is applied to top 43b of p.c. board 43. IR radiation emitted by lamp 53 is thus reflected on the inside of reflector 54 and reflective substrate coating 59 and is able to reach gas sensor module 1 through substrate opening 54—if necessary, after multiple reflections. The vertical height of reflector 54 in this case is largely determined by the height of lamp 53, which is designed, for example, as a low-current incandescent light bulb. Additional structural components are advantageously not provided on top 43b of substrate 43; in particular there are no electronic components.

What is claimed is:

1. A gas sensor module for a spectroscopic measurement of at least one gas concentration, comprising:
    a spectroscopic gas sensor having a sensor chip which has a micropatterned measuring structure and contact pads, and having an IR-transparent cap chip which is attached to the sensor chip and covers the measuring structure;
    a premolded package, injection-molded from one of a plastic material and a molding compound and having a package bottom and a package edge to which a cover, having a screen opening situated above the measuring structure, is attached;
    a filter chip situated between the cover and the cap chip for selectively filtering an infrared spectral range; and
    a lead frame which is partially injected into the premolded package and has multiple leads whose outer areas are connecting pins for contacting a substrate and whose inner areas are contact pads which are contacted with the contact pads of the gas sensor, the connecting pins being bent upward from the package edge.

2. The gas sensor module according to claim 1, wherein the connecting pins each have a first lower curvature via which the leads emerging from the package edge are bent upwards, and a second upper curvature via which the leads are bent outward in a substantially horizontal direction.

3. The gas sensor module according to claim 1, further comprising a conductive shielding plate connected to at least one of the leads and injected into the package bottom beneath the gas sensor.

4. The gas sensor module according to claim 1, wherein the filter chip is attached to the cap chip beneath the screen opening.

5. The gas sensor module according to claim 1, wherein the contact pads of the leads and the contact pads of the gas sensor are bond pads which are contacted with one another via wire bonds.

* * * * *